United States Patent [19]

Debras et al.

[11] Patent Number: 4,599,473

[45] Date of Patent: Jul. 8, 1986

[54] PROCESS FOR PARA SELECTIVE ALKYLATION OF AROMATIC HYDROCARBONS

[75] Inventors: Guy L. G. Debras, Belgrade; Georges E. M. J. De Clippeleir, Sint Pieters Leeuw; Raymond M. Cahen, Brussels, all of Belgium

[73] Assignee: Cosden Technology, Inc., Dallas, Tex.

[21] Appl. No.: 562,650

[22] Filed: Dec. 19, 1983

[51] Int. Cl.[4] ............................................. C07C 2/68
[52] U.S. Cl. ..................................................... 585/467
[58] Field of Search ......................................... 585/467

[56] References Cited

U.S. PATENT DOCUMENTS

| | | | |
|---|---|---|---|
| 4,368,114 | 1/1983 | Chester et al. | 208/120 |
| 4,370,508 | 1/1983 | Kaeding | 585/467 |
| 4,387,260 | 6/1983 | Watson et al. | 585/467 |

OTHER PUBLICATIONS

Wu et al, *The Journal of Physical Chemistry*, vol. 83, No. 21, 1979, pp. 2777-2781.

*Primary Examiner*—Curtis R. Davis
*Attorney, Agent, or Firm*—William D. Jackson; John K. Abokhair; M. Norwood Cheairs

[57] ABSTRACT

A process for the selective alkylation of monoalkylbenzene into dialkylbenzenes wherein the para isomer of the disubstituted product is present in a concentration greater than in a thermodynamic equilibrium is provided.

The method comprises passing the monoalkylbenzene and an alkylating agent capable of methylation, ethylation or propylation through a reaction zone containing an unmodified crystalline silica catalyst of the silicalite type having the monoclinic symmetry.

14 Claims, No Drawings

PROCESS FOR PARA SELECTIVE ALKYLATION OF AROMATIC HYDROCARBONS

TECHNICAL FIELD

This invention relates to a process for the production of dialkyl benzenes employing silicalite type catalysts having monoclinic symmetry. More specifically, a process is provided for the selective alkylation of monoalkyl-benzenes, such as toluene and ethylbenzene, over a silicalite type catalyst having catalytic activity, and in particular activity toward alkylating in the para position to the existing alkyl group on the substituted benzene to yield a dialkyl benzene product in which the para isomer is present in an amount greater than would be present in a thermodynamic equilibrium isomer mix.

BACKGROUND ART

Various dialkyl benzenes, such as ethyltoluene and diethyl benzene, are used as important precursor compounds from which the corresponding vinyl aromatic monomers are made. The resulting monomers, i.e., vinyltoluene and divinylbenzene, are essential to the production of a variety of styrenic polymer materials. Additionally, xylene is a useful dialkyl benzene used in the production of terephthalic acid which is an important intermediate in the synthesis of polyester fibers and films.

In the case of diethylbenzene and ethyltoluene, the para isomer is the most useful intermediate, with the ortho isomer being highly undesirable. Because of the undesirability of the ortho isomer, expensive distillation techniques must be employed prior to dehydrogenation of the ethyltoluene and diethylbenzene.

At present, many alkylbenzene conversion processes include processing steps wherein the aromatic substrates which are to be converted are contacted under conversion conditions in the presence of catalysts. Both single and multiple bed catalyst processes are well known in the art. An important property to be considered in the selection of the catalyst is the selectivity of the catalyst to the desired product. A subcategory of the selectively of the catalyst to the desired product is the selectivity of the catalyst to the desired isomer of the desired product, for example, "para-selectivity".

Various aluminosilicate type zeolite catalysts, including those known as "ZSM" catalysts, have been reported to be suitable for selectively producing para substituted benzene derivatives upon being modified for that purpose. One problem with these types of catalysts, however, is that they are subject to rapid deactivation in the presence of even small amounts of water. Rapid deactivation means that a high rate of conversion of reactants to products cannot be maintained over a long period of time thus requiring expensive catalyst change-outs or regeneration procedures which greatly reduce the efficiency of the overall process. Thus, in using such catalysts it is sometimes necessary to reduce the moisture content of the feed stock materials prior to their introduction to a conversion zone.

Another problem with the aforementioned aluminosilicate type catalysts is that they must often be modified with "promoters" to obtain significantly increased para-selectivity. In other words, these types of catalysts have little or no intrinsic para-selectivity, i.e. the catalysts must be modified before they will produce a product in which the para isomer is present in an amount greater than in a thermodynamic equilibrium. The thermodynamic equilibrium concentration for isomers of ethyltoluene is about 31.5% para, about 50.2% meta and about 18.3% ortho at normal operating conditions for vapor phase alkylation.

More recently, catalysts characterized as crystalline silica polymorphs prepared in accordance with specified procedures and known generally as "silicalite" type catalysts, have been discovered to be useful in aromatic conversion processes. It has already been disclosed that these catalysts have intrinsic para-selective properties. It would therefore be most useful to have a catalyst showing even more para-selectivity, even in the presence of steam.

As noted earlier, the para isomer of the dialkylbenzenes is the most useful intermediate, with the ortho isomer being the most undesirable. A need exists, therefore, for a process for selectively producing para dialkylbenzenes in amounts greater than that present in a thermodynamic equilibrium.

SUMMARY OF THE INVENTION

An object of the present invention is to provide an improved process for the selective alkylation of monoalkylbenzenes into dialkylbenzenes wherein the para isomer is present in an amount greater than that contained in a thermodynamic equilibrium mix.

Another object of the present invention is to provide an improved process according to which an enhanced selectivity for the para isomer is provided and simultaneously high rates of conversion are maintained during long periods of time.

Still another object of the present invention is to provide a process wherein a silicalite type catalyst is used, said catalyst having the monoclinic symmetry and possessing enhanced intrinsic para-selective properties, without requiring special promotion or "selectivation treatments".

In accordance with the present invention, a process is provided for the selective alkylation of monoalkylbenzene into dialkylbenzenes wherein the para isomer of the disubstituted product is present in a concentration greater than in a thermodynamic equilibrium mix, said process comprising passing the monoalkylbenzene and an alkylating agent capable of methylation, ethylation or propylation under conversion conditions through a reaction zone containing an unmodified crystalline silica catalyst of the silicalite type having the monoclinic symmetry.

The process of the present invention comprises contacting the reactants to be converted under conversion conditions in the presence of a crystalline silica catalyst of the silicalite type having the monoclinic symmetry. In a preferred embodiment of the present invention, aromatic substrates such as toluene and ethylbenzene are alkylated with an alkylating agent, such as methanol, ethylene or propylene, by contacting the aromatic substrate and alkylating agent under alkylation conditions in the presence of a crystalline silica catalyst of the silicalite type having the monoclinic symmetry. Said catalyst material need not be modified in any manner and water in the form of steam may be present in the feed.

By operating at temperatures ranging between 350° C. and 500° C. and in the presence of steam, the paraselectivity and the activity of the unmodified crystalline silica catalyst having the monoclinic symmetry can be maintained.

DETAILED DESCRIPTION

In accordance with the present invention, a process is provided for selective alkylation of monoalkylbenzenes to produce a dialkyl benzene product in which the para isomer is present in an amount greater than in a thermodynamic equilibrium mix. The process essentially comprises feeding the monoalkyl benzene and an alkylating agent under controlled conversion conditions to a reaction zone containing a crystalline silica catalyst of the silicalite type having the monoclinic symmetry. The monoalkyl benzene is either toluene or ethylbenzene and the alkylating agent can be any alkylating agent capable of effecting methylation, ethylation or propylation under conversion conditions. The desired dialkyl products generally produced are xylene, diethylbenzene, ethyltoluene, propyltoluene. In one preferred embodiment, the monoalkyl benzene is toluene, the alkylating agent is ethylene and the dialkyl product, therefore, is ethyltoluene.

The process of the present invention can be carried out using a variety of process equipment, including a reactor vessel having a hydrocarbon conversion zone which contains the abovementioned catalyst having the monoclinic symmetry. Either single or multiple catalyst beds can be employed in the reaction zone. The reactants can be admixed and preheated prior to introduction into the reaction zone where they contact the catalyst bed(s) under conversion conditions further specified hereinbelow. Steam may be admixed with the reactants just prior to their introduction into the reaction zone. After a controlled residence time within the reaction zone, the converted hydrocarbon charge passes out of the reactor where the desired products are collected by cooling or other standard recovery techniques.

The mole ratio of hydrocarbon reactants will be controlled in accordance with the desired reaction products. Pressures and weight hourly space velocities of the reactants passing through the conversion zone will be the major factors effecting residence time (and, therefore, contact time with the catalyst of the invention having the monoclinic symmetry) within the zone. The temperatures specified herein are measured as an average inlet temperature of the conversion zone during steady state operation.

The catalyst material employed by the process of the subject invention is a crystalline silica material as opposed to a zeolitic material, which, can be represented by the general formula $M_{2/n}O.Al_2O_3.xSiO_2yH_2O$, M being cation of valence n, generally sodium. The materials used as catalysts in the present invention are crystalline silicas of the silicalite type having the monoclinic symmetry which will be further referenced as monoclinic catalyst. Aluminum may be present in the monoclinic catalyst as a result of impurity in the silica source used to prepare the catalyst.

In addition to the physical distinction between the monoclinic catalyst and more conventional aluminosilicate zeolites, several functional distinctions are also apparent as regards the use of these materials as hydrocarbon conversion catalysts. For example, ZSM-type aluminosilicate zeolites are reported to rapidly lose their catalytic activity in the presence of even minor amounts of water. As noted hereinabove, the monoclinic catalysts of the present invention are useful hydrocarbon conversion catalysts even in the presence of steam. Further, the monoclinic catalysts utilized in the process of the present invention exhibit enhanced intrinsic paraselective properties and need not be modified in order to produce a dialkyl product in which the para isomer is present in an amount greater than in a thermodynamic equilibrium mix.

Thus the catalysts useful in the present invention are unmodified in the sense that no special chemical, thermal or steam pretreatment of the catalyst as synthesized is necessary prior to its use in the described process.

According to an embodiment of the present invention, monoclinic catalysts may be produced by treating a non-calcined crystalline silica polymorph, as described in U.S. Pat. No. 4,061,724, the entire disclosure of which is incorporated herein by reference, said uncalcined silica polymorph will be further referenced to as raw silicalite.

The raw silicalite used in the process of the present invention may contain aluminum as impurity but in an amount such that the silica to alumina atomic ratio lies above 80:1.

The treatment of said raw silicalite, a detailed description of which has been given in the co-pending application Ser. No. 562,652 entitled "Process for Preparing Crystalline Silicas" consists in calcining at a temperature above 500° C. during a sufficient period of time to obtain monoclinic symmetry of the calcined material. The calcined material is further washed with ammonium nitrate solution and dried at 300° C. for 3 hours. The dried material retains its monoclinic symmetry. It is further mixed with an appropriate amount of a suitable binding material to make catalyst pellets or extrudates, these latter being finally calcined at 500° C. under nitrogen flow. If aluminum hydroxide is used as binding material, it is well understood that the aluminum so introduced is not to be considered in the silica to alumina atomic ratio of raw silicalite. This latter calcination may directly be carried out in situ during the start-up period of the alkylation process of the invention.

It is understood that monoclinic catalysts have a definite X-ray diffraction pattern. Among the significant characteristics which distinguish monoclinic catalysts from non-monoclinic catalysts, one of them is the appearance of doublet at the interplanar spacing of about $d = 3.65 \pm 0.02$ Å.

Other features of the X-ray diffraction pattern which may be used to distinguish the monoclinic catalysts of the invention from the others may be exemplified by the appearance of doublet at the interplanar spacing of d=3.05 to 3.06 Å and a singlet peak appears at the interplanar spacing of about d=3.00+0.02 Å.

A typical X-ray pattern (Cobalt Kα radiation) of monoclinic catalyst is given herebelow.

| Interplanar Spacing d (Angstroms) | Relative Intensity |
| --- | --- |
| 11.33 | 100 |
| 10.18 | 52 |
| 9.89 | 22 |
| 6.76 | 10 |
| 6.41 | 16 |
| 6.05 | 20 |
| 5.74 | 11 |
| 5.61 | 14 |
| 5.17 | 3 |
| 5.06 | 7 |
| 5.01 | 8 |
| 4.38 | 9 |
| 4.28 | 11 |
| 4.10 | 5 |
| 4.03 | 7 |
| 3.87 | 82 |
| 3.83 | 42 |
| 3.77 | 22 |
| 3.73 | 48 |
| 3.67 | 15 |
| 3.64 | 15 |
| 3.61 | 4 |
| 3.50 | 5 |
| 3.46 | 7 |
| 3.41 | 4 |
| 3.37 | 7 |
| 3.33 | 7 |
| 3.32 | 11 |
| 3.27 | 5 |
| 3.15 | 3 |
| 3.06 | 6 |
| 3.05 | 6 |
| 3.00 | 15 |
| 2.95 | 7 |
| 2.74 | 4 |
| 2.69 | 3 |
| 2.60 | 3 |
| 2.52 | 4 |
| 2.49 | 5 |
| 2.42 | 4 |
| 2.02 | 10 |
| 2.00 | 9 |
| 1.88 | 3 |

In a preferred embodiment, toluene feedstock is alkylated by contacting same with ethylene in the presence of monoclinic catalyst under conversion conditions. Conversion inlet temperatures should range between about 300° C. and 600° C., with temperatures of between about 370° C. and 450° C. being preferred. Surprisingly, it has been discovered that the para-selectivity of the monoclinic catalyst is enhanced as compared to ZSM-type aluminosilicate catalysts. By employing these conditions, increased selectivity, as measured by the amount of alkylating agent converted to the desired para dialkyl substituted benzene products, is obtained and improved stability can be achieved when steam is co-fed. It has been found that in the presence of steam, by contrast to ZSM-type aluminosilicate catalyst, the catalyst used in the process of the invention leads to improved para-selective properties.

Generally, the reaction of monoalkyl benzene feedstock with alkylating agents is run with a substantial molar excess of monoalkyl benzene in order to reduce the incidence of polyalkylation. Preferred reactant molar ratios are from about 2:1 to about 20:1, monoalkyl benzene:alkylating agent. Pressure of from about atmospheric to about 25 atmospheres can be employed with preferred monoalkyl benzene weight hourly space velocity (WHSV) of from about 50 to about 250. Higher WHSV, providing greater kinetic control of the process, may also be useful.

The process of the subject invention, which employs monoclinic catalysts, provides an especially efficient procedure for producing para-ethyltoluene, para-diethylbenzene, para-xylene and para-propyltoluene. When employing the subject process to produce ethyltoluene from toluene feedstock, the preferred monoclinic catalysts are those having a crystallite size of less than about ten microns and a silica to alumina atomic ratio not lower than 80 and preferably higher than about 120.

Preferred reactant ratios are between about 7:1 and 18:1, with the preferred monoalkyl benzene WHSV ranging from about 100 to about 200. Further operating conditions include a pressure range of from about 10 to 15 atmospheres. Inlet temperatures within the preferred range of from about 350° C. to about 450° C. are also employed.

In the process of the invention, steam is generally co-fed. The preferred amount of steam is from about 20,000 to about 60,000 parts per million, based on the amount of aromatic compound, preferably from about 30,000 to about 50,000 parts per million.

The process of the present invention can be further exemplified through a study of the following examples which are not intended to limit the subject invention in any manner.

EXAMPLE 1

Toluene and ethylene are introduced into a reaction zone containing a bed of 3 ml of monoclinic catalyst material having a particle size of between 35 and 45 meshes. This catalyst has been prepared by taking a raw (uncalcined) silicalite having a diffraction pattern in accordance with that disclosed in U.S. Pat. No. 4,061,724. The material has a silica to alumina atomic ratio of 130 and crystallite sizes comprised between 1 and 3 microns. It has further been calcined for 72 hours at 600° C. in the presence of air. The diffraction pattern of the cooled product has shown that the material has a monoclinic symmetry as shown by the peak at d=3.65 Å. The cooled catalyst material was further treated with an 0.1N ammonium nitrate solution, dried for 3 hours at 300° C.; the dried product was then mixed with 20% by weight of Condea SB alumina as a binder, further pressed to make tablets which were ground and sieved into the 35–45 mesh fraction used in the reaction zone. The catalyst was further calcined in the reactor under nitrogen flow at 500° C.

The alkylation of toluene by ethylene into ethyltoluene has been carried out at the following operating conditions:

Inlet temperature: about 400° C.

Pressure: 15 kg/cm$^2$
Toluene WHSV: 194
Toluene:ethylene mole ratio: 8.1
Water:toluene mole ratio: 0.2
(approximately 40,000 ppm water on toluene)

The product stream from the alkylation reaction zone is analyzed by gas chromatography. The catalyst activity is determined according to the following formula:

$$\% \text{ conversion} = \frac{\text{moles of alkylating agent reacted}}{\text{moles of alkylating agent fed to reactor}} \times 100$$

The para-selectivity is determined according to the following formula:

$$\frac{\text{para dialkylaromatic compound}}{\text{meta dialkylaromatic compound}},$$

at a given conversion as defined above.

The results obtained are indicated in Table 1 (Ex. 1).

EXAMPLE 2

Toluene and ethylene are introduced into a reaction zone containing a bed of 3 ml of monoclinic catalyst having a particle size between 35 and 45 meshes.

This catalyst has been prepared from the same raw silicalite as described in Example 1.

It has further been calcined for 3 hours at 600° C. in the presence of air. As in Example 1, the resulting material had the monoclinic symmetry.

The catalyst is further treated as described in Example 1; after loading it to the reactor it is calcined under nitrogen flow at 420° C.

The alkylation of toluene by ethylene into ethyltoluene has been carried out at the following operating conditions:
Mean catalyst bed temperature: 419°–425° C.
Pressure: 15 kg/cm$^2$
Toluene WHSV: 191–194
Toluene:ethylene mole ratio: 8.1
Water:toluene mole ratio: 0.2
(about 40,000 ppm water on toluene)

The obtained results are indicated in Table 1 (Ex. 2). By way of comparison, the same raw silicalite catalyst has been calcined for 1 hour at 500° C. in the presence of air and the X-ray diffraction pattern has shown this material to be of the non-monoclinic symmetry.

Further treatments of the catalyst material are identical to those described for the first catalyst tested in Example 2. The range of alkylating conditions are very similar to those hereabove given for the first catalyst tested.

The results are given in Table 1 (Ex. 2A).

EXAMPLE 3

Toluene and ethylene are introduced into a reaction zone containing a bed of 3 ml of monoclinic catalyst having a particle size of between 35 and 45 meshes.

This catalyst has been prepared by taking a raw silicalite having a diffraction pattern in accordance with that disclosed in U.S. Pat. No. 4,061,724.

This material has a silica to alumina atomic ratio of 450 and crystallite sizes comprised between 4 and 6 microns.

It has further been calcined for 10 hours at 600° C. in the presence of air. The diffraction pattern of the cooled product has shown that the material had the monoclinic symmetry as shown by the presence of a doublet at d=3.65 Å.

The catalyst is further treated as described in Example 1. After loading it to the reactor, it is calcined under nitrogen flow at 500° C.

The alkylation of toluene by ethylene into ethyltoluene has been carried out at the following operating conditions:
Inlet temperature: 410° C.
Pressure: 15 kg/cm$^2$
Toluene WHSV: 187.5
Toluene:ethyltoluene mole ratio: 8.1
Water:toluene mole ratio: 0.2
(about 40,000 ppm of water)

The obtained results are indicated in Table 1 (Ex. 3). By way of comparison, the same raw silicalite catalyst has been calcined for 1 hour at 475° C. in the presence of air and the X-ray diffraction pattern has shown this material to be of the non-monoclinic symmetry.

Further treatments of the catalyst material are identical to those described for the first catalyst tested in this Example 3. The range of alkylating conditions are the same as those hereabove given for the first catalyst tested.

The results are given in Table 1 (Ex. 3A).

This example clearly shows the advantage of catalysts of the monoclinic symmetry over those of the non-monoclinic symmetry.

TABLE 1

|  | Conversion % | toluene: ethylene mole ratio | water: toluene mole ratio | selectivity para/ meta | ortho isomer content |
| --- | --- | --- | --- | --- | --- |
| Ex. 1 | 70 | 8.1 | 0.2 | 6.0 | not detected |
| Ex. 2 | 70 | 8.1 | 0.2 | 4.8 | not detected |
| Ex. 2A | 70 | 8.1 | 0.2 | 2.4 | not detected |
| Ex. 3 | 55 | 8.1 | 0.2 | 7.4 | not detected |
| Ex. 3A | 55 | 8.1 | 0.2 | 2.5 | not detected |

The results indicated in this table clearly show the superiority of the monoclinic catalysts over those which do not have the monoclinic symmetry, particularly when steam is present.

While the present invention has been described in various embodiments and illustrated by numerous examples, the person of ordinary skill in the art will appreciate that various modifications, substitutions, omissions, and changes may be made without departing from the spirit thereof, such modifications may be exemplified by the fact that the monoclinic catalyst may be impregnated with various elements such as, for instance, arsenic, phosphorus, boron, magnesium, nickel, palladium, and platinum.

What we claim is:

1. A process for the selective alkylation of monoalkylbenzene into dialkylbenzenes wherein the para isomer of the disubstituted product is present in a concentration greater than in a thermodynamic equilibrium, comprising:

passing the monoalkylbenzene and an alkylating agent capable of methylation, ethylation or propylation under conversion conditions through a reaction zone containing an unmodified crystalline silica catalyst of the silicalite type having the monoclinic symmetry.

2. The process according to claim 1 further comprising co-feeding steam with the monoalkylbenzene and alkylating agent through the reaction zone.

3. The process according to claim 1 wherein the alkylating agent is ethylene.

4. The process according to claim 1 wherein the alkylating agent is methanol.

5. The process according to claim 1 wherein the alkylating agent is propylene.

6. The process according to claim 1 wherein the monoalkylbenzene is toluene.

7. The process according to claim 1 wherein the monoalkylbenzene is ethylbenzene.

8. The process according to claim 1 wherein the conversion conditions comprise temperatures in the range of from about 300° C. to about 600° C., a molar feed ratio of monoalkylbenzene to alkylating agent between about 2:1 and about 20:1, a monoalkylbenzene WHSV ranging from about 50 to about 250 and pressures ranging from about atmospheric to about 25 atmospheres.

9. The process according to claim 8 wherein the temperature range is from about 350° C. to about 450° C., the molar feed ratio is from about 7:1 to about 18:1, the pressure range is from about 10 to about 15 atmospheres, and the monoalkylbenzene WHSV range is from about 100 to about 200.

10. The process according to claim 2 wherein the steam is present in an amount of from about 20,000 to about 60,000 parts per million based on the weight of monoalkylbenzene employed.

11. The process according to claim 10 wherein the steam is present in an amount comprised between 30,000 and 50,000 parts per million based on the weight of monoalkylbenzene employed.

12. The process according to claim 1 wherein the crystalline silica catalyst of the silicalite type having the monoclinic symmetry has a silica to alumina atomic ratio not lower than 80:1.

13. The process according to claim 12 wherein the crystalline silica catalyst of the silicalite type has a doublet at the interplanar spacing of about $d = 3.65 \pm 0.02$ Å of its X-ray pattern.

14. A process for producing dialkylbenzene products comprising:
   (a) introducing to a reaction zone containing a bed of crystalline silica catalyst of the silicalite type having the monoclinic symmetry, a monoalkylbenzene and an alkylating agent;
   (b) allowing said monoalkylbenzene and alkylating agent to come into contact with said catalyst under conversion conditions; and
   (c) recovering from said reaction zone a dialkyl benzene isomer mix comprising a greater than thermodynamic equilibrium amount of the para isomer thereof.

* * * * *